(12) United States Patent
Lynch et al.

(10) Patent No.: US 7,220,238 B2
(45) Date of Patent: *May 22, 2007

(54) SHUNT DEVICE AND METHOD FOR TREATING GLAUCOMA

(75) Inventors: Mary G. Lynch, Atlanta, GA (US); Reay H. Brown, Atlanta, GA (US); Stuart Ball, Mobile, AL (US)

(73) Assignee: GMP Vision Solutions, Inc., Fort Lauderdale, FL (US)

( * ) Notice: Subject to any disclaimer, the term of this patent is extended or adjusted under 35 U.S.C. 154(b) by 82 days.

This patent is subject to a terminal disclaimer.

(21) Appl. No.: 10/899,687

(22) Filed: Jul. 27, 2004

(65) Prior Publication Data

US 2005/0038334 A1 Feb. 17, 2005

Related U.S. Application Data

(63) Continuation of application No. 10/222,209, filed on Aug. 16, 2002, which is a continuation-in-part of application No. 09/558,505, filed on Apr. 26, 2000, now Pat. No. 6,450,984.

(60) Provisional application No. 60/312,799, filed on Aug. 16, 2001, provisional application No. 60/131,030, filed on Apr. 26, 1999.

(51) Int. Cl.
*A61M 37/00* (2006.01)

(52) U.S. Cl. .......................................................... 604/8

(58) Field of Classification Search ................ 64/8–10, 64/264, 523, 284, 289, 521; 606/107–108; 623/4.1, 1.11, 1.1, 1.35
See application file for complete search history.

(56) References Cited

U.S. PATENT DOCUMENTS

| 3,788,327 | A | * | 1/1974 | Donowitz et al. | ........... 604/247 |
| 5,868,697 | A | * | 2/1999 | Richter et al. | ................. 604/8 |
| 6,827,699 | B2 | * | 12/2004 | Lynch et al. | .................... 604/8 |

* cited by examiner

*Primary Examiner*—Patricia Bianco
(74) *Attorney, Agent, or Firm*—Lott & Friedland, P.A.; Michael J. Keller

(57) ABSTRACT

The present invention provides a shunt for the flow of aqueous humor from the anterior chamber of the eye to Schlemm's canal. The device comprises at least one lumen and optionally has at least one anchor extending from the proximal portion within the anterior chamber to assist in placement and anchoring of the device in the correct anatomic position.

23 Claims, 10 Drawing Sheets

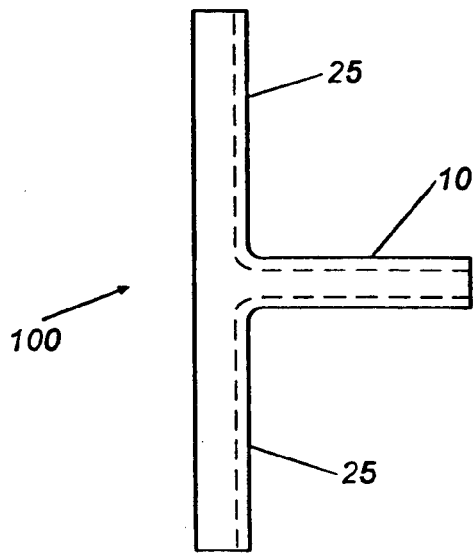
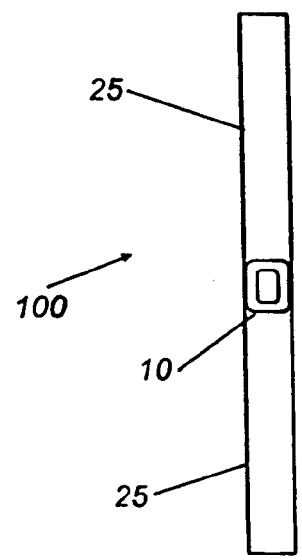
Fig. 3B     Fig. 3C
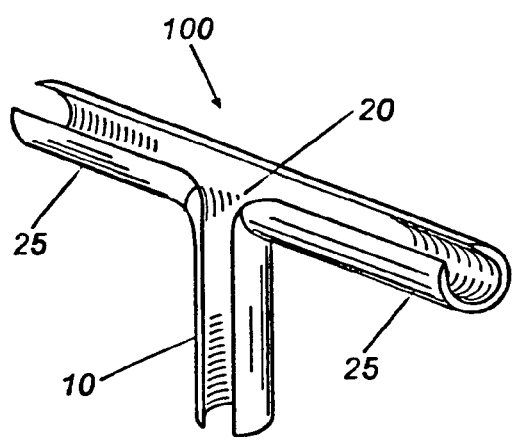
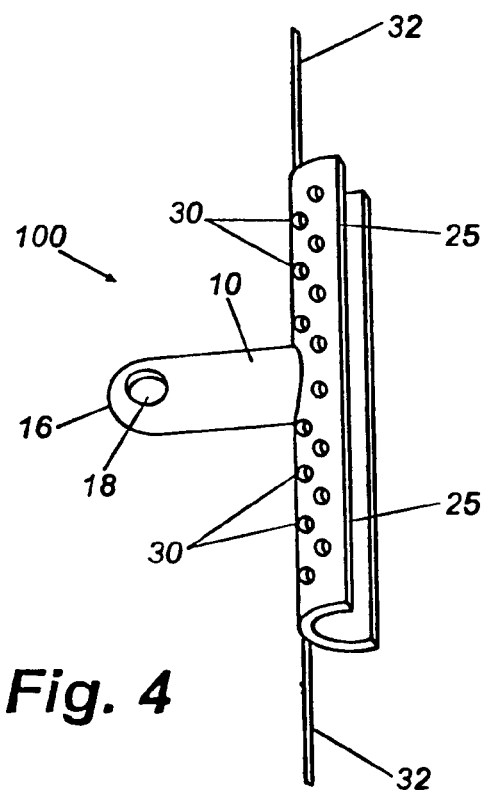
Fig. 3D     Fig. 4

SHUNT DEVICE AND METHOD FOR TREATING GLAUCOMA

CROSS REFERENCE TO RELATED APPLICATIONS

This application is a Continuation of U.S. application Ser. No. 10/222,209, filed Aug. 16, 2002, which claims the benefit of U.S. Provisional Application Ser. No. 60/312,799 filed Aug. 16, 2001 and is a Continuation-In-Part of U.S. application Ser. No. 09/558,505, filed Apr. 26, 2000, now U.S. Pat. No. 6,450,984, which claims the benefit of U.S. Provisional Application No. 60/131,030, filed Apr. 26, 1999.

GOVERNMENT LICENSE

The U.S. Government has reserved a nonexclusive, irrevocable, royalty-free license in the invention with power to grant licenses for all governmental purposes.

BACKGROUND OF THE INVENTION

1. Field of the Invention

The present invention is generally directed to a surgical treatment for glaucoma, and relates more particularly to a device and method for continuously decompressing elevated intraocular pressure in eyes affected by glaucoma by diverting aqueous humor from the anterior chamber of the eye into Schlemm's canal where post-operative patency can be maintained with an indwelling shunt which can be surgically placed to connect the canal with the anterior chamber.

2. Background Art

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's Canal is believed to be divided by septa into a series of autonomous, dead-end canals.

The aqueous fluid travels through the spaces between the trabecular beams, across the inner wall of Schlemm's canal into the canal, through a series of about 25 collecting channels that drain from Schlemm's canal and into the episcleral venous system. In a normal situation, aqueous production is equal to aqueous outflow and intraocular pressure remains fairly constant in the 15 to 21 mmHg range. In glaucoma, the resistance through the canalicular outflow system is abnormally high.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is not long lasting and fifty percent of patients develop an elevated pressure within five years. The laser surgery is not usually repeatable. In addition, laser trabeculoplasty is not an effective treatment for primary open angle glaucoma in patients less than fifty years of age, nor is it effective for angle closure glaucoma and many secondary glaucomas. If laser trabeculoplasty does not reduce the pressure enough, then filtering surgery is performed. With filtering surgery, a hole is made in the sclera and angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected half-thickness into the cornea. The anterior chamber is entered beneath the scleral flap and a section of deep sclera and trabecular meshwork is excised. The scleral flap is loosely sewn back into place. The conjunctival incision is tightly closed. Post-operatively, the aqueous fluid passes through the hole, beneath the scleral flap and collects in an elevated space beneath the conjunctiva. The fluid then is either absorbed through blood vessels in the conjunctiva or traverses across the conjunctiva into the tear film.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases.

Trabeculectomy creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. The risk increases with the thin blebs that develop after MMC and 5-FU. Another factor that contributes to infection is the placement of a bleb. Eyes that have trabeculectomy performed inferiorly have about five times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Patients with blebs generally cannot wear contact lenses. All of the complications from trabeculectomy stem from the fact that fluid is being diverted from inside the eye to the external surface of the eye.

When trabeculectomy doesn't successfully lower the eye pressure, the next surgical step often is an aqueous shunt device. An aqueous diversion device of the prior art is a silicone tube that is attached at one end to a plastic (polypropylene or other synthetic) plate. With an aqueous shunt device, an incision is made in the conjunctiva, exposing the sclera. The plastic plate is sewn to the surface of the eye posteriorly, usually over the equator. A full thickness hole is made into the eye at the limbus, usually with a needle. The tube is inserted into the eye through this hole. The external portion of the tube is covered with either donor sclera or pericardium. The conjunctiva is replaced and the incision is closed tightly.

With prior art aqueous diversion devices, aqueous drains out of the eye through the silicone tube to the surface of the eye. Deeper orbital tissues then absorb the fluid. The outside end of the tube is protected from fibroblasts and scarring by the plastic plate. Many complications are associated with aqueous shunt devices. A thickened wall of scar tissue that develops around the plastic plate offers some resistance to outflow and in many eyes limits the reduction in eye pressure. In some eyes, hypotony develops because the flow through the tube is not restricted. Many physicians tie an absorbable suture around the tube and wait for the suture to dissolve post-operatively at which time enough scar tissue has hopefully formed around the plate. Some devices contain a pressure-sensitive valve within the tube, although these valves may not function properly. The surgery involves operating in the posterior orbit and many patients develop an eye muscle imbalance and double vision post-operatively. With prior art aqueous shunt devices, a pathway is created for bacteria to get into the eye and endophthalmitis can potentially occur.

The prior art includes a number of such aqueous shunt devices, such as U.S. Pat. No. 4,936,825 (providing a tubular shunt from the anterior chamber to the corneal surface for the treatment of glaucoma), U.S. Pat. No. 5,127,901 (directed to a transscleral shunt from the anterior chamber to the subconjunctival space), U.S. Pat. No. 5,180,362 (teaching a helical steel implant that is placed to provide drainage from the anterior chamber to the subconjunctival space), and U.S. Pat. No. 5,433,701 (generally teaching shunting from the anterior chamber to the scleral or conjunctival spaces).

In addition to the prior art aqueous shunt devices described above, other prior art devices for glaucoma surgery have used setons, or other porous, wick-like components to divert and convey excess aqueous from the anterior chamber to the exterior ocular surface. Examples include U.S. Pat. Nos. 4,634,418 and 4,787,885 (teaching the surgical treatment of glaucoma using an implant that consists of a triangular seton (wick)), and U.S. Pat. No. 4,946,436, (teaching the use of a porous device to shunt anterior chamber to subscleral space). These patents do not teach placement in Schlemm's canal.

Some prior art references for glaucoma management have been directed at Schlemm's canal, but these have not involved the placement of long-term, indwelling shunts. U.S. Pat. No. 5,360,399 teaches the temporary placement of a plastic or steel tube with preformed curvature in Schlemm's canal with injection of a viscous material through the tube to hydraulically expand and hydrodissect the trabecular meshwork. The tube is removed from the canal following injection. Because the tube is directed outwardly from the eye for injection access, the intersection of the outflow element with the preformed curved element within Schlemm's canal is at about a 90 degree angle relative to the plane of the curvature, and 180 degrees away from the anterior chamber. Therefore, at no time does any portion of the '399 device communicate with the anterior chamber. Furthermore, relative to that portion within Schlemm's canal, this tube has a larger diameter injection cuff element, which serves as an adapter for irrigation. Therefore, this device is not adapted for shunting aqueous between the anterior chamber and Schlemm's canal.

Most of the problems that have developed with current glaucoma treatment devices and procedures have occurred because aqueous fluid is drained from inside of the eye to the surface of the eye. A need exists, then, for a more physiologic system to enhance the drainage of aqueous fluid from the anterior chamber into Schlemm's canal. In the vast majority of glaucoma patients, the resistance problem lies between Schlemm's canal and the anterior chamber. The canal itself, the collecting channels and the episcleral venous system all are intact. Enhancing aqueous flow directly into Schlemm's canal would minimize the scarring that usually occurs with external filtration procedure since the internal angle region is populated with a single line of nonproliferating trabecular cells. Enhancing aqueous flow directly into Schlemm's canal would minimize hypotony since the canal is part of the normal outflow system and is biologically engineered to handle the normal volume of aqueous humor. Enhancing aqueous flow directly into Schlemm's canal would eliminate complications such as endophthalmitis and leaks.

SUMMARY OF THE INVENTION

The present invention is directed to a novel shunt and an associated surgical method for the treatment of glaucoma in which the shunt is placed to divert aqueous humor from the anterior chamber of the eye into Schlemm's canal. The present invention therefore facilitates the normal physiologic pathway for drainage of aqueous humor from the anterior chamber, rather than shunting to the sclera or another anatomic site as is done in most prior art shunt devices. The present invention is further directed to providing a permanent, indwelling shunt to provide increased egress of aqueous humor from the anterior chamber to Schlemm's canal for glaucoma management.

BRIEF DESCRIPTION OF THE DRAWINGS

FIG. 3B is an illustration showing a top view of the embodiment of the present invention in FIG. 3A, with phantom lines detailing the internal communication of the device.

FIG. 3C is an illustration showing a side view from the proximal end of the embodiment of the present invention in FIG. 3A.

FIG. 3D is an illustration showing a perspective of another embodiment of the present invention in which the inventive shunt is comprised of elements that are partially open and trough-like in their configuration.

FIG. 4 is an illustration showing another embodiment of the present invention, in which the inventive shunt is comprised of distal elements having wicking extensions at their terminal ends, and in which the proximal portion has a sealed, blunted tip with a portal continuous with the lumen of the proximal portion, oriented to face away from the iris when the device is implanted in Schlemm's canal.

DETAILED DESCRIPTION OF THE INVENTION

Figure 1A:
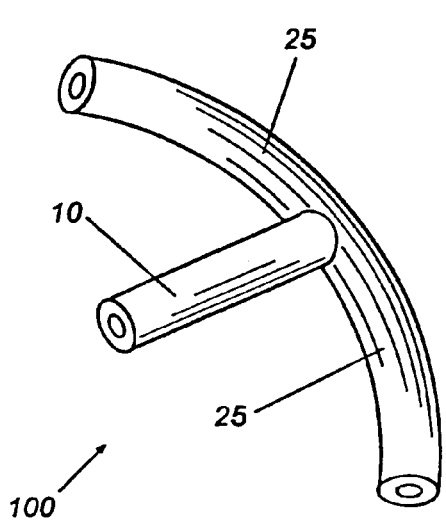
FIG. 1A is an illustration showing an overhead perspective view of one embodiment of the present invention, in which the inventive shunt is comprised of tubular elements extending bi-directionally within Schlemm's canal.

The present invention provides an aqueous humor shunt device to divert aqueous humor in the eye from the anterior chamber into Schlemm's canal, in which the shunt device comprises a distal portion having at least one terminal aspect sized and shaped to be circumferentially received within a portion of Schlemm's canal, and a proximal portion having at least one terminal aspect sized and shaped to be received within the anterior chamber of the eye, wherein the device permits fluid communication between the proximal portion in the anterior chamber to the distal portion in Schlemm's canal. Fluid communication can be facilitated by an aqueous humor directing channel in either the proximal or distal portions, as described below. Fluid communication can also be facilitated by a wicking function of a solid proximal or distal portions of the device, for example.

The present invention also provides embodiments of an inventive shunt comprising a body of biocompatible material of a size and shape adapted to be at least partially circumferentially received within a portion of Schlemm's canal to divert aqueous humor from the anterior chamber of the human eye to and within Schlemm's canal, and wherein the body facilitates the passage of aqueous humor from the anterior chamber into Schlemm's canal. This embodiment of the device of the present invention can be produced without the proximal portion of the previous embodiment extending into the anterior chamber. An aqueous humor directing channel can facilitate the passage of aqueous humor from the anterior chamber into Schlemm's canal. Fluid communication can also be facilitated by a wicking function of a solid body portion, for example.

The invention contemplates many different configurations for an aqueous humor directing channel, provided that each assists in channeling aqueous humor from the anterior chamber to Schlemm's canal, such as by providing a lumen, trough, wick or capillary action. For example, the aqueous humor directing channel can be a fully enclosed lumen, a partially enclosed lumen, or a trough-like channel that is at least partially open. The invention contemplates that a solid monofilament or braided polymer, such as Proline® (polypropylene), can be inserted into Schlemm's canal to provide a wicking or stenting function to facilitate the passage of aqueous humor from the anterior chamber to Schlemm's canal. Such a wicking or stenting extension can also be grooved or fluted along any portion of the length thereof, so as to be multi-angular or star-shaped in cross-section. The devices of the present invention can be constructed of a solid, matrix, mesh, fenestrated, or porous material, or combinations thereof.

Traditional glaucoma teaching states that Schlemm's canal in an adult is divided by septa into separate canals, rendering the complete passage of a suture impossible. Preliminary studies on adult human eye bank eyes have shown that Schlemm's canal is, indeed, patent. A suture can be passed through the entire circumference of the canal. It has not been heretofore determined that Schlemm's canal is patent throughout its circumference in normal adult individuals, as opposed to being divided by septa into multiple dead end canals. The invention utilizes this knowledge to access Schlemm's canal and to create and maintain the natural physiologic egress of aqueous humor from the anterior chamber to Schlemm's canal and to the collecting channels.

The present invention also provides methods of use of the shunt devices. One embodiment of the present invention is directed to a surgical method to divert aqueous humor from the anterior chamber of the eye into Schlemm's canal with a device that is implanted to extend from within the anterior chamber to Schlemm's canal. The portion of the device extending into Schlemm's canal can be fashioned from a flexible material, such as silicone, capable of being received within a portion of the radius, curvature, and diameter of Schlemm's canal. The external diameter of the proximal portion can be about 0.1 mm to 0.5 mm, or about 0.3 mm. Preliminary studies indicate a preferred diameter for the proximal portion to be about 0.23 mm to about 0.28 mm, or preferably about 0.23 mm to about 0.26 mm. All or parts of the device may be solid, porous, tubular, trough-like, fenestrated, or pre-curved.

Figure 1B:
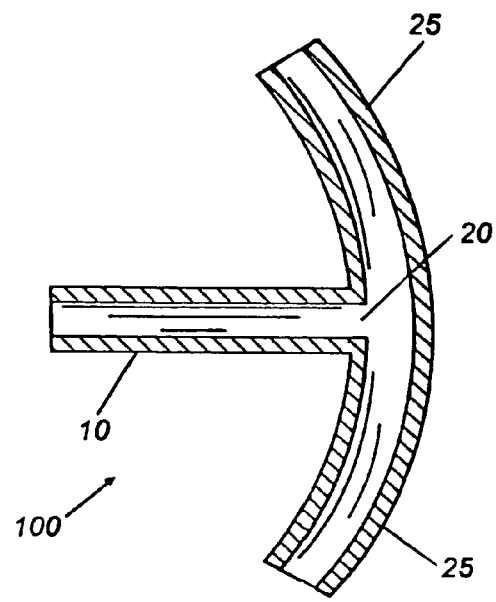
FIG. 1B is an overhead view of the embodiment of the present invention shown in FIG. 1A, with phantom lines detailing the internal communication between the lumens of the tubular elements comprising the inventive device.

One embodiment of the present invention is illustrated in FIG. 1A, in which the shunt device 100 is shown in a side view. The shunt device 100 of this embodiment is comprised of two portions, a proximal portion 10 which joins a distal portion 25. The proximal portion 10 and distal portion 25 shown create an enclosed tubular channeling structure. The total length of the distal portion 25 may be between about 1.0 mm to 40 mm, preferably about 4 mm to 6 mm. The same embodiment of the present invention is illustrated with phantom lines showing the internal fluid communication path in FIG. 1B. The lumen or channeling space defined by the walls of the proximal portion 10 and the distal portion(s) 25 are continuous at their junction at the distal portion portal 20.

Figure 1C:
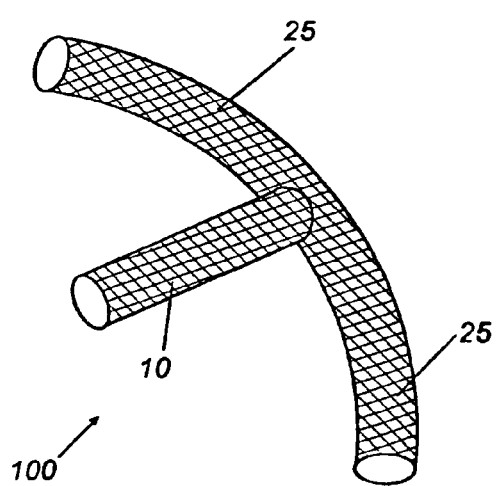
FIG. 1C is an illustration showing an overhead perspective view of one embodiment of the present invention, in which the inventive shunt is comprised of mesh tubular elements extending bi-directionally within Schlemm's canal.
Figure 1D:
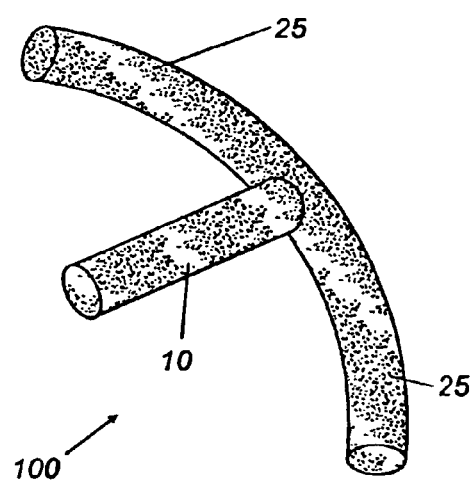
FIG. 1D is an illustration showing an overhead perspective view of one embodiment of the present invention, in which the inventive shunt is comprised of solid, porous elements extending bi-directionally within Schlemm's canal.

An alternate embodiment of the present invention is shown in FIG. 1C, in which the shunt device 100 is comprised of two luminal mesh elements, with a proximal portion 10 which joins a distal portion 25. Yet another embodiment of the present invention is shown in FIG. 1D, in which the shunt device 100 is comprised of two solid, porous elements which may provide wick-like fluid communication therethrough, with a proximal portion 10 which joins a distal portion 25.

Figure 1E:
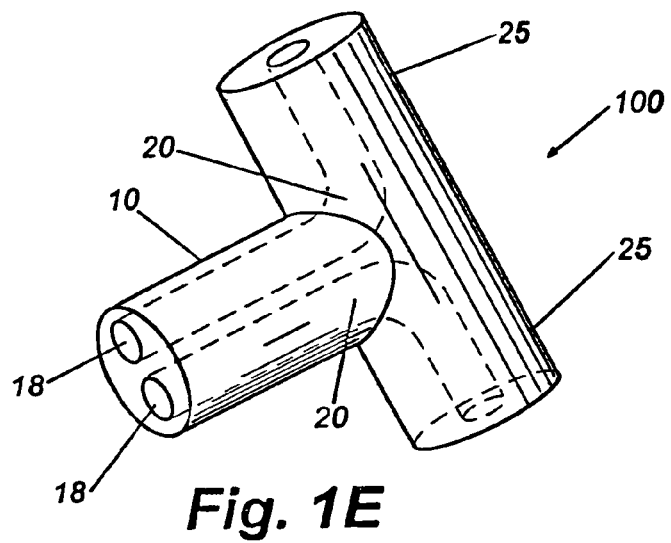
FIG. 1E is an overhead perspective view of another embodiment of the present invention, with phantom lines detailing the internal communication between the two proximal lumens and the single distal lumen of the inventive device.

An alternate embodiment of the present invention is shown in FIG. 1E, in which the shunt device 100 is comprised of a proximal portion 10 having two lumens therein terminating in proximal portion portals 18. The distal portion 25 shaped and sized to be received within Schlemm's canal extends in either direction having separate lumens traversing therethrough from each of the distal portion portals 20.

Figure 2:
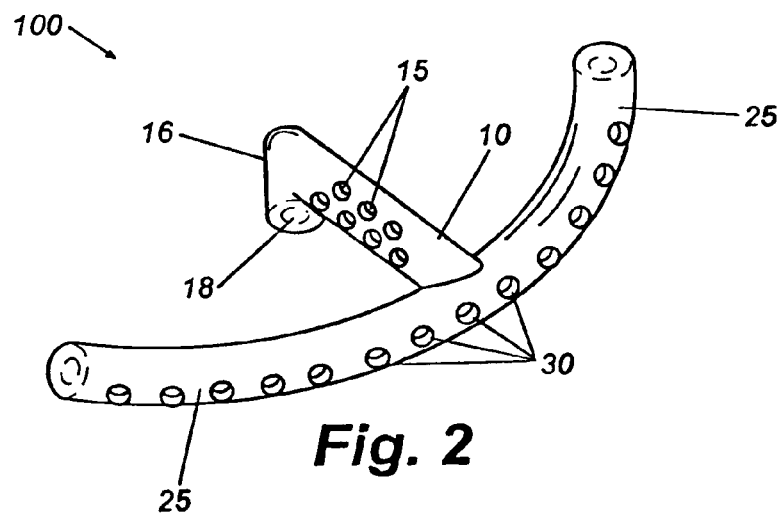
FIG. 2 is an illustration showing another embodiment of the present invention, in which the inventive shunt is comprised of perforated tubular elements and with an angulated terminal aspect of the proximal portion.

Other examples of embodiments of the present invention are shown in FIGS. 2-5D. FIG. 2 shows an embodiment of the inventive shunt in which the device 100 is tubular and fenestrated (15, 30) in its configuration, with an acute (<90) angle of junction between the proximal portion 10 and the plane defined by the distal portion 25. Such fenestrations (15, 30) may be placed along any portion of the device 100 to facilitate the passage of fluid therethrough, but are particularly directed towards the collecting channels of the eye. FIG. 2 further shows an alternate embodiment of the present invention in which the terminal aspect 16 of the proximal portion is angulated toward the iris 40 with respect to the main axis of the proximal portion 10, with the portal 18 of the proximal portion directed toward from the iris 40. In alternate embodiments as shown in FIG. 6C, the portal 18 of the proximal portion 16 is directed away from the iris 40.

Figure 3A:
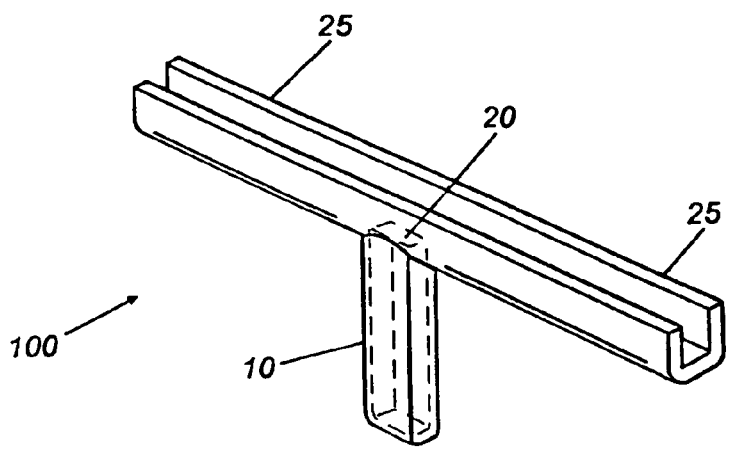
FIG. 3A is an illustration showing a perspective of another embodiment of the present invention in which the inventive shunt is comprised of elements that are partially tubular and partially open in their configuration.

FIG. 3A shows an embodiment of the inventive shunt in which a portion of the channeling device is enclosed and tubular in configuration at the junction of the proximal portion 10 and the distal portion 25, but where the distal portion 10 is a trough-like channel. The distal portion portal 20 is also shown. The invention contemplates that any portion of the device 100 can be semi-tubular, open and trough-like, or a wick-like extension. Tubular channels can be round, ovoid, or any other enclosed geometry. Preferably the non-tubular trough-like aspects are oriented posteriorly on the outer wall of the canal to facilitate aqueous humor drainage to the collecting channels of the eye, as shown in FIG. 3A.

FIG. 3B shows an overhead view of the embodiment of the inventive shunt of FIG. 3A, further detailing the relationship among the proximal portion 10 and the distal portion 25. The aqueous humor directing channel is shown in dashed lines. FIG. 3C shows a proximal view of the embodiment of the inventive shunt of FIG. 3A, further detailing the relationship among the proximal portion 10 and the distal portion 25.

FIG. 3D shows another embodiment of the inventive shunt in which the structure of the device 100 comprises an aqueous humor directing channel that is both open and curved in a continuous trough-like configuration along the proximal portion 10 and the distal portion 25. The distal portion portal 20 is also an open trough-like channel.

FIG. 4 shows another embodiment of the inventive shunt with the addition of aqueous humor-wicking extensions 32 which are either continuous with, or attached to the terminal aspects of the distal portion 25. The wicking extensions 32 can be fashioned from a monofilament or braided polymer, such as proline, and preferably have a length of about 1.0 mm to about 16.0 mm. Furthermore, the proximal portion 10 is curved with a sealed, blunted tip 16 and contains a portal 18 in fluid communication with the lumen of the proximal portion and oriented to face away from the iris when the shunt device 100 is implanted in its intended anatomic position. The shunt device 100 can also help to maintain the patency of Schlemm's canal in a stenting fashion.

Figure 5A:
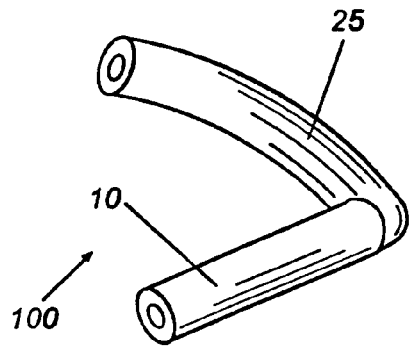
FIG. 5A is an illustration showing another embodiment of the inventive shunt in which a portion of the device enters Schlemm's canal in only one direction and shunts fluid in a non-linear path from the anterior chamber.

FIG. 5A shows another embodiment of the inventive shunt in which the proximal portion 10 joins a single, curved distal portion 25 in a "V-shaped," tubular configuration. The embodiment shown in FIG. 5A can also have a portal (not shown) in the distal portion 25 adjacent to the junction with the proximal portion 10 in order to facilitate bi-directional flow of fluid within the canal. Fenestrations and non-tubular, trough-like terminal openings are contemplated in all embodiments of the invention, and these fenestrations and openings may be round, ovoid, or other shapes as needed for optimum aqueous humor channeling function within the anatomic spaces involved.

Figure 5B:
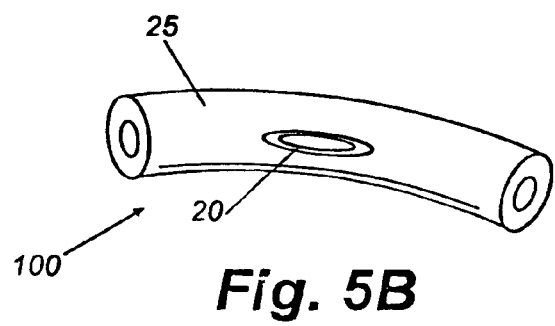
FIG. 5B is an illustration showing an alternative embodiment of the inventive shunt in which the entire shunt is placed within Schlemm's canal but contains a fenestration to maintain fluid egress of aqueous humor from the anterior chamber to Schlemm's canal.

FIG. 5B shows another embodiment of the inventive shunt in which the body or device 100 comprises only a single, curved distal portion 25 which contains a distal portion portal 20 oriented towards the anterior chamber to allow egress of aqueous humor from the anterior chamber to Schlemm's canal. The body of this device can have a length of about 1.0 mm to about 40 mm, preferably about 6 mm. The external diameter of the device (or the distal portions of the device) can be about 0.1 mm to about 0.5 mm, preferably about 0.2 mm to about 0.3 mm, preferably about 0.23 mm to about 0.28 mm or about 0.26 mm.

Figure 5C:
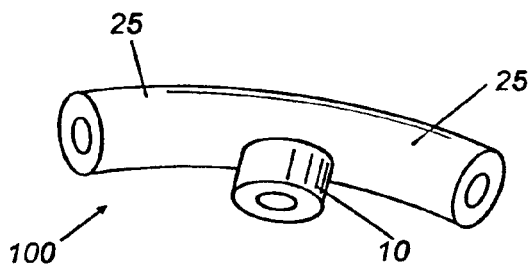
FIG. 5C is an illustration showing a side view of one embodiment of the present invention, in which the inventive shunt is comprised of tubular elements, with a proximal portion extending towards the anterior chamber that is shorter relative to the distal portions which extend bi-directionally within Schlemm's canal.

FIG. 5C shows another embodiment of the inventive shunt in which the device 100 comprises a bi-directional tubular distal portion 25 which is intersected by a proximal portion 10 which is short in length relative to the distal portion 25 and is directed towards the anterior chamber.

Figure 5D:
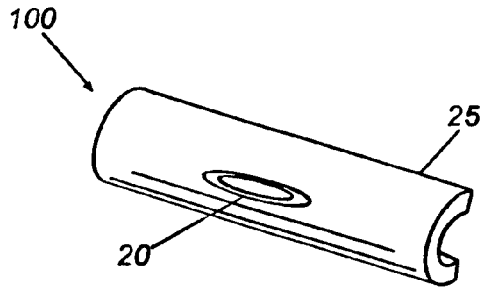
FIG. 5D is an illustration showing an alternative embodiment of the inventive shunt comprised of a partially open trough-like element which is placed within Schlemm's canal but contains a portal to maintain fluid egress of aqueous humor from the anterior chamber to Schlemm's canal.

FIG. 5D shows still another embodiment of the inventive shunt in which the device 100 comprises a bi-directional, trough-like, curved distal portion 25 for insertion into Schlemm's canal, which contains a distal portion portal 20 oriented to allow egress of aqueous humor from the anterior chamber, wherein the trough-like distal portion 25 is oriented to open toward the collecting channels to facilitate the egress of aqueous humor.

Figure 5E:
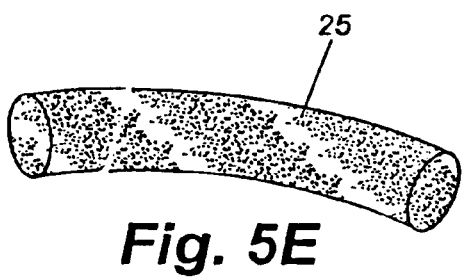
FIG. 5E is an illustration showing an alternative embodiment of the inventive shunt comprised of a solid, but porous wick-like element which is placed within Schlemm's canal

FIG. 5E shows another embodiment of the inventive shunt in which the device 100 comprises a bi-directional, solid distal portion 25 for insertion into Schlemm's canal to facilitate the egress of aqueous humor from the canal to the collecting channels in a wicking capacity. The solid distal portion 25 can be porous or non-porous.

As the inventive device is an implant, it can be fabricated from a material that will be compatible with the tissues and fluids with which it is in contact. The device may be constructed of biodegradable or non-biodegradable materials. It is preferable that the device not be absorbed, corroded, or otherwise structurally compromised during its in situ tenure. Moreover, it is equally important that the eye tissues and the aqueous remain non-detrimentally affected by the presence of the implanted device. A number of materials are available to meet the engineering and medical specifications for the shunts. In the exemplary embodiments of the present invention, the shunt device 100 is constructed of a biologically inert, flexible material such as silicone or similar polymers. Alternate materials might include, but are not limited to, thin-walled Teflon®, polypropylene, other polymers or plastics, metals, or some combination of these materials. The shunt device 100 may be constructed as either porous or solid in alternate embodiments. The material can contain a therapeutic agent deliverable to the adjacent tissues.

In the embodiments shown in FIGS. 1-4, the proximal portion 10 joins the distal portion(s) 25 at an angle sufficient to allow the placement of the proximal portion 15 within the anterior chamber of the eye when the distal portion 25 is oriented in the plane of Schlemm's canal. The proximal portion 10 is preferably of sufficient length, about 0.1 to about 3.0 mm or about 2.0 mm, to extend from its junction with the distal portion 25 in Schlemm's canal towards the adjacent space of the anterior chamber. While many geometries can be used for channeling aqueous humor, the diameter or width of the proximal portion 10 can be sized to yield an internal diameter of between about 0.1 and about 0.5 mm, preferably about 0.2 mm to about 0.3 mm for a tubular or curved shunt, or a comparable maximal width for a shunt with a multiangular configuration. In other embodiments, the proximal portion is a non-luminal, non-trough-like wicking extension that provides an aqueous humor directing channel along the length thereof.

Because the nature of the iris 40 is such that it tends to comprise a plurality of rather flaccid fimbriae of tissue, it is desirable to avoid said fimbriae from being drawn into the lumen of an implant, thus occluding the shunt device.

Therefore, the proximal portion 10 may contain a plurality of fenestrations to allow fluid ingress, arranged to prevent occlusion by the adjacent iris. Alternately, the proximal portion 10 may comprise only a proximal portion portal 18 in the form of a fenestration oriented anteriorly to provide continuous fluid egress between the anterior chamber of the eye and the directing channel of the shunt. Said fenestrations may be any functional size, and circular or non-circular in various embodiments of the present invention. In addition, a porous structural material can assist in channeling aqueous humor, while minimizing the potential for intake of fimbriae.

Furthermore, the proximal portion 10 may be positioned sufficiently remote from the iris 40 to prevent interference therewith, such as by traversing a more anterior aspect of the trabecular meshwork into the peripheral corneal tissue. In yet another possible embodiment, as shown in FIG. 6C, the device 100 may comprise a proximal portion 10 in which the terminal aspect of said proximal portion 10 is curved or angled toward the iris 40, and with a blunted, sealed tip 16 and a portal 18 oriented anteriorly to face away from the underlying iris 40. Such a configuration would tend to decrease the possibility of occlusion of the shunt device by the iris 40.

The device 100 may contain one or more unidirectional valves to prevent backflow into the anterior chamber from Schlemm's canal. The internal lumen for an enclosed portion of the device or the internal channel defined by the edges of an open portion of the device communicates directly with the inner lumen or channel of the distal portion at the proximal portion portal 20.

The distal portion 25 may have a pre-formed curve to approximate the 6.0 mm radius of Schlemm's canal in a human eye. Such a pre-formed curvature is not required when flexible material is used to construct the shunt device 100. The distal portion 25 may be of sufficient length to extend from the junction with the proximal portion 10 through any length of the entire circumference of Schlemm's canal. Embodiments having a distal portion 25 that extends in either direction within Schlemm's canal can extend in each direction about 1.0 mm to 20 mm, or about 3.0 mm. to permit circumferential placement through Schlemm's canal. The diameter or width of the distal portion 25 can be sized to yield an outer diameter of between about 0.1 and 0.5 mm, or about 0.3 mm, for a tubular or curved shunt, or a comparable maximal width for a shunt with a multiangular configuration. The distal portion 25 may contain a plurality of fenestrations to allow fluid egress, arranged to prevent occlusion by the adjacent walls of Schlemm's canal. In other embodiments, the distal portion is a non-luminal, non-trough-like wicking extension that provides an aqueous humor directing channel along the length thereof.

In the exemplary embodiments of the present invention, the shunt device may be either bi-directional, with the distal portion of the implant intersecting with the proximal portion in a "T-shaped" junction as shown in FIGS. 1A-1E, 2, 3A-3D, 4 and 5C, or uni-directional, with a "V-shaped" junction of the proximal and distal shunt portions, as shown in FIG. 5A. A bi-directional shunt device can have a distal portion that is threaded into opposing directions within Schlemm's canal. In the case of the uni-directional shunt, only the distal shunt portion is placed within Schlemm's canal. In these exemplary embodiments, "non-linear fluid communication" means that at least some portion of the shunt through which fluid passes is not in a straight line. Examples of non-linear shunts are the above described bi-directional "T" shapes, and the uni-directional "V" shapes, or shunts having two channel openings which are not in straight alignment with each other when implanted.

Figure 6A:
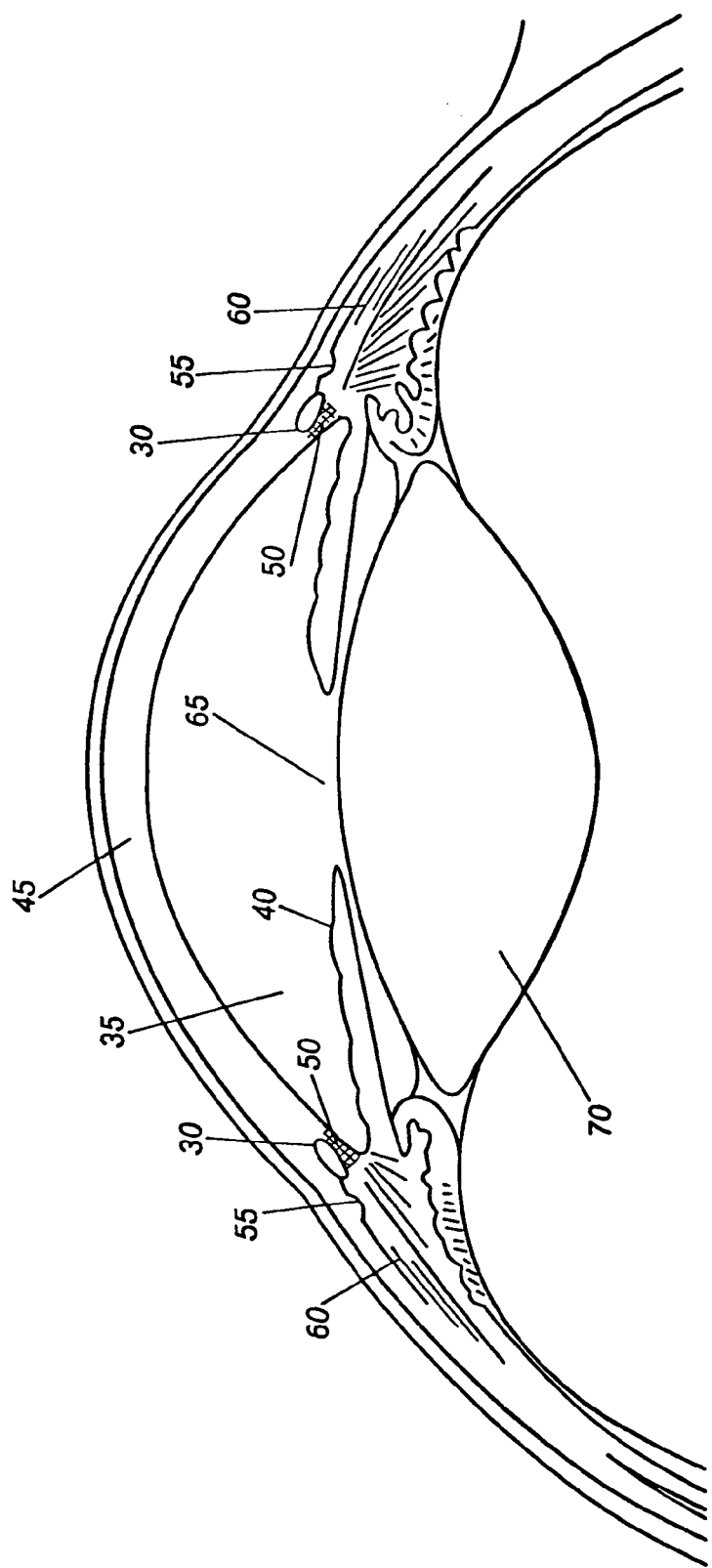
FIG. 6A is an illustration showing certain anatomic details of the human eye.
Figure 6B:
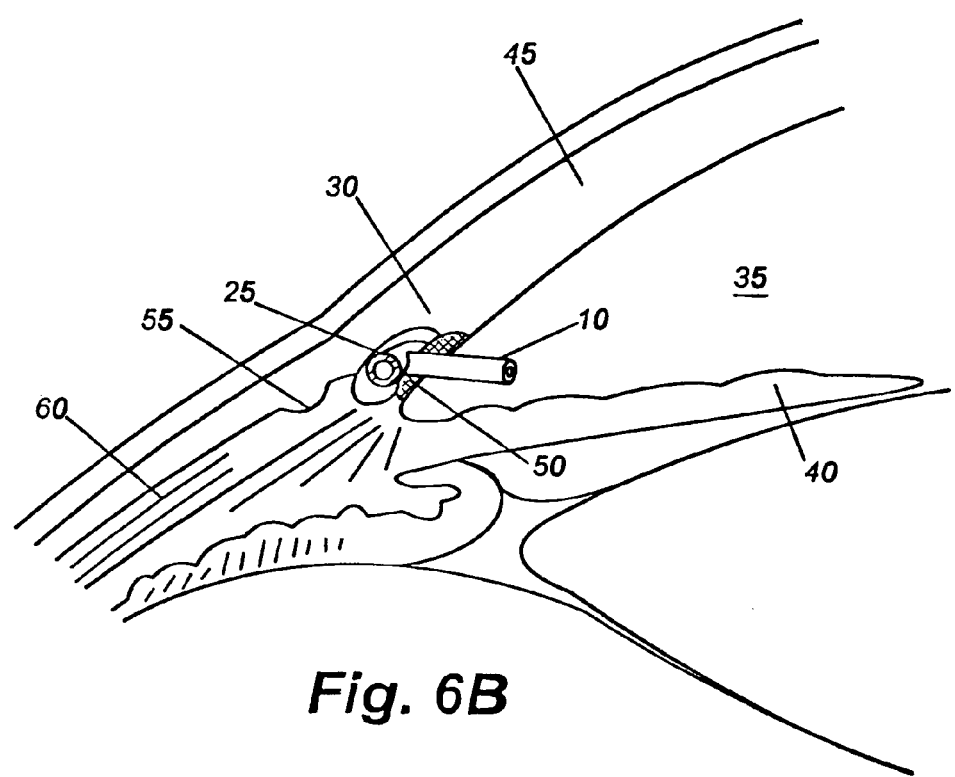
FIG. 6B is a cross-sectional illustration showing the anatomic relationships of the surgical placement of an exemplary embodiment of the present invention.
Figure 6C:
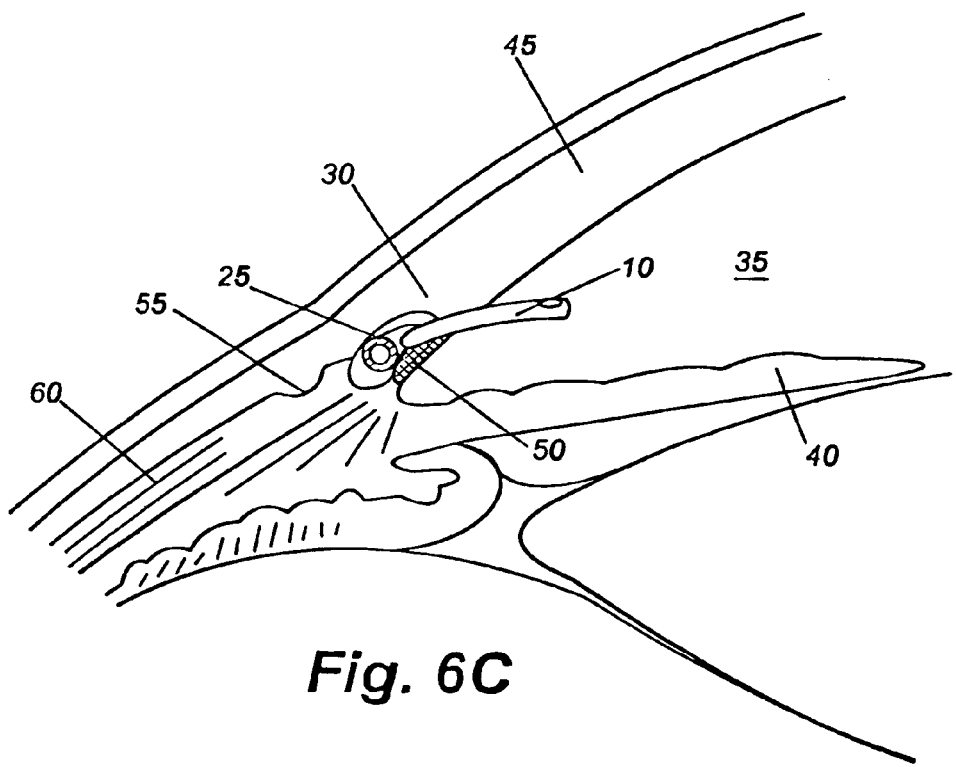
FIG. 6C is a cross-sectional illustration showing the anatomic relationships of the surgical placement of another exemplary embodiment of the present invention in which the proximal portion has an angulated terminal aspect with a sealed, blunted tip with a portal continuous with the lumen of the proximal portion, oriented to face away from the iris when the device is implanted in Schlemm's canal.

The surgical anatomy relevant to the present invention is illustrated in FIG. 6A. Generally, FIG. 6A shows the anterior chamber 35, Schlemm's canal 30, the iris 40, cornea 45, trabecular meshwork 50, collecting channels 55, episcleral veins 60, pupil 65, and lens 70. FIG. 6B illustrates the surgical placement of the exemplary embodiment of the present invention, with the relevant anatomic relationships. It should be noted that the inventive device is designed so that placement of the distal portion 25 within Schlemm's canal 30 results in an orientation of the proximal portion 10 within the anterior chamber 35 within the angle defined by the iris 40 and the inner surface of the cornea 45. Therefore, if the plane defined by Schlemm's canal is defined as zero degrees, the proximal portion 10 can extend therefrom at an angle of between about +60 degrees towards the cornea 45 or −30 degrees toward the iris 40, more preferably in the range of 0 to +45 degrees. This range may vary in individuals having a slightly different location of Schlemm's canal 30 relative to the limbal angle of the anterior chamber 35.

In yet another embodiment of the present invention not shown, the shunt device 100 is configured with one distal portion 25 which is tubular to provide a shunting functionality and a plurality of proximal portions 10 which provide an anchoring function to stabilize the overall implant device, in addition to providing fluid communication from the anterior chamber to Schlemm's Canal.

Therefore, the invention provides an aqueous humor shunt device to divert aqueous humor in an eye from the anterior chamber into Schlemm's canal, the shunt device comprising a distal portion having at least one terminal aspect sized and shaped to be received circumferentially within a portion of Schlemm's canal and a proximal portion having at least one terminal aspect sized and shaped to be received within the anterior chamber of the eye, wherein the proximal portion has an anchor extending therefrom to maintain the position of the terminal aspect of the proximal portion within the anterior chamber of the eye, wherein device permits fluid communication from the proximal portion in the anterior chamber to the distal portion in Schlemm's canal. In alternative embodiments, such an anchor can extend from distal portions of the device to assist in stabilization of the implant within Schlemm's canal.

The multiple proximal portions or the anchor extension(s) from the distal or proximal portion (collectively referred to as the "anchor") in the various embodiments described below and apparent to those of skill in the art in view of the present disclosure, provide multiple improvements for the shunt device. The anchor facilitates implantation and proper placement of the device, as the proximal portion can be advanced into the anterior chamber and then pulled back into place until it contacts the edge of the anterior chamber. As further described below, a shelf may be created by the surgical procedure for implantation that is designed to capture the anchor. This permits the surgeon to determine how much of the proximal portion is left extending into the anterior chamber. The anchor feature also allows the surgical alternative of first implanting the proximal portion into the anterior chamber, and then placing the distal portion(s) into Schlemm's canal. The anchor also serves to anchor the shunt device in the desired location within the anterior chamber and Schlemm's canal with minimal shifting during normal use.

Figure 7A:
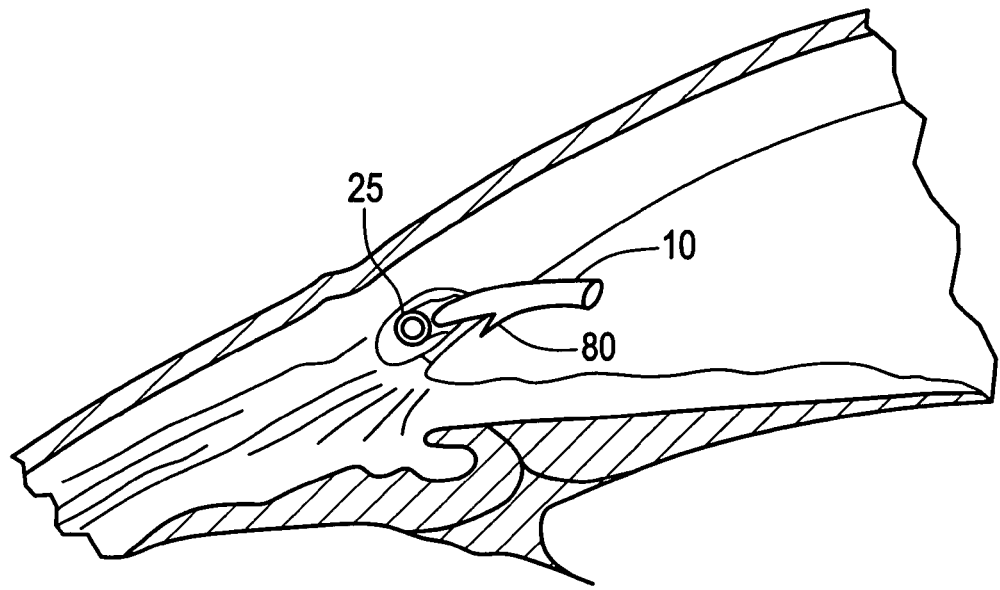
FIG. 7A is a cross-sectional illustration showing the anatomic relationships of the surgical placement of an exemplary embodiment of the present invention showing the proximal portion of the device and a barb-shaped anchor extending toward the iris.
Figure 7B:
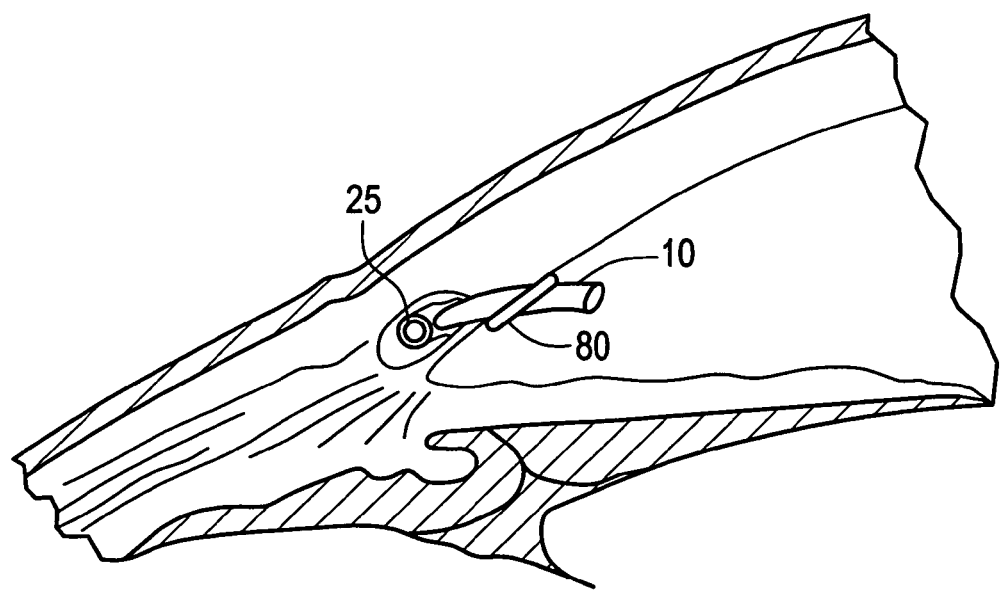
FIG. 7B is a cross-sectional illustration showing the anatomic relationships of the surgical placement of another exemplary embodiment of the present invention showing the proximal portion of the device having an annular or circumferential anchor thereon.

The anchor can be fabricated by a simple thickening of the material of construction of the shunt, e.g. silicon, at the desired site on the proximal portion, or can be made of another material attached thereto. Additionally, the anchor can be fabricated by removal of excess material. The anchor can extend from the proximal portion in virtually any functional shape, such as in a rounded or barbed fashion. FIG. 7A is a cross-sectional illustration showing the anatomic relationships of the surgical placement of an exemplary embodiment of the present invention showing the proximal portion 10 of the device and a barb-shaped anchor 80 extending toward the iris. FIG. 7B is a cross-sectional illustration showing the anatomic relationships of the surgical placement of another exemplary embodiment of the present invention showing the proximal portion 10 of the device having an annular or circumferential anchor 80 thereon.

Figure 8A:
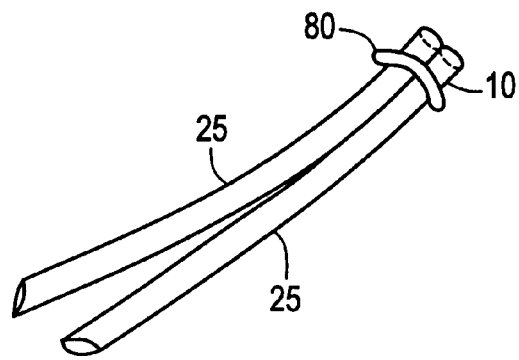
FIG. 8A shows one embodiment of the device having a bi-directional distal portion and an anchor on the proximal portion extending circumferentially thereon.
Figure 8B:
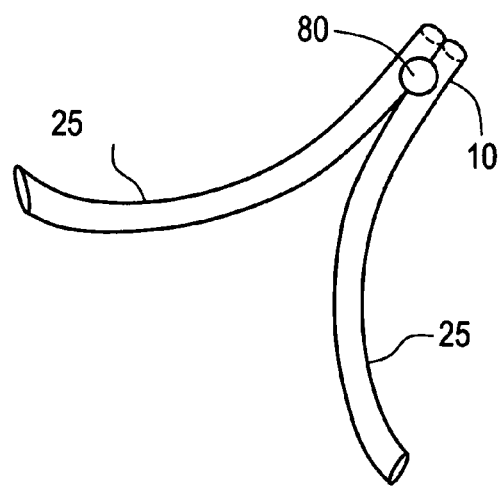
FIG. 8B shows another embodiment of the device having a bi-directional distal portion and an anchor on the proximal portion extending medially toward the location of the iris when implanted.
Figure 8C:
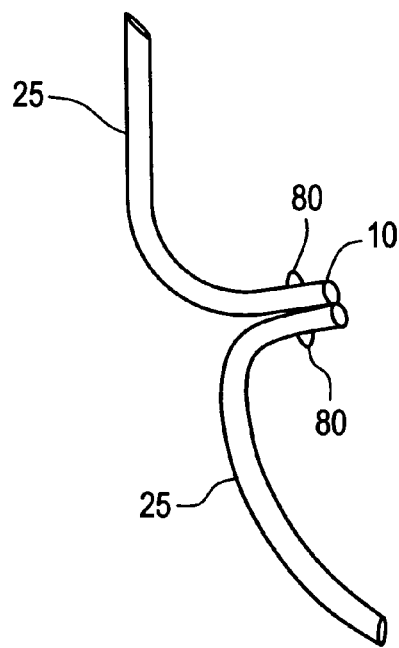
FIG. 8C shows another embodiment of the device having a bi-directional distal portion and an anchor on the proximal portion extending laterally on each side of the device when implanted.

Therefore, the anchor can extend circumferentially around the proximal portion, or only in one or more directions therefrom. FIG. 8A shows one embodiment of the device having a bi-directional distal portion 25 and an anchor 80 on the proximal portion 10 extending circumferentially thereon. FIG. 8B shows another embodiment of the device having a bi-directional distal portion 25 and an anchor 80 on the proximal portion 10 extending medially toward the location of the iris when implanted. FIG. 8C shows another embodiment of the device having a bi-directional distal portion 25 and an anchor 80 on the proximal portion 10 extending laterally on each side of the device when implanted. The invention contemplates many other configurations of the anchor, including a plurality of teeth extending from the proximal portion.

The device may also be provided with an anchor for placement adjacent the exterior surface of the anterior chamber to assist in surgical placement and securing the device, with or without a corresponding anchor adjacent the interior surface of the anterior chamber. Thus, a potential configuration to stabilize the implant is a device having anchors for positioning inside the anterior chamber and inside Schlemm's canal to secure the device about the trabecular meshwork between the anterior chamber and Schlemm's canal.

Figure 9:
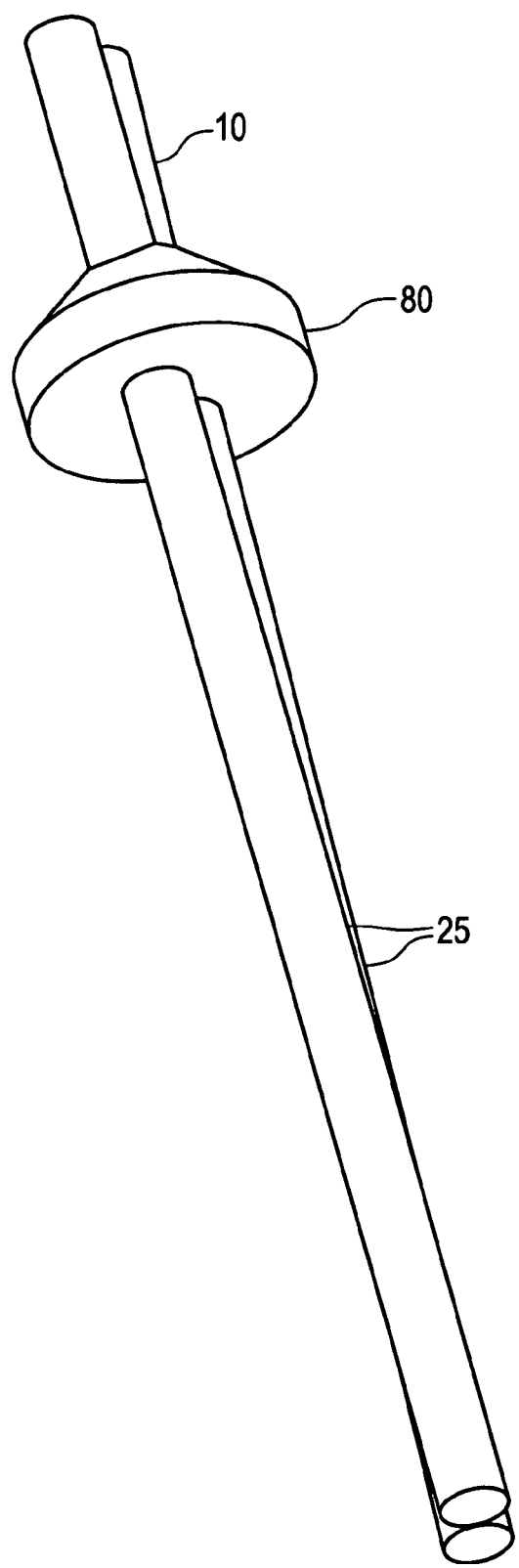
FIG. 9 shows another embodiment having a bi-directional distal portion and an anchor on the proximal portion extending circumferentially thereon in a barbed or cone shape to facilitate introduction into the anterior chamber and to inhibit removal therefrom.

It is understood that the anchor can extend in any direction in any shape and size which facilitates implantation or anchoring of the device. For example, FIG. 9 shows another embodiment having a bi-directional distal portion 25 and an anchor 80 on the proximal portion 10 extending circumferentially thereon in a barbed or cone shape to facilitate introduction into the anterior chamber and to inhibit removal therefrom. Furthermore, the end of the proximal portion can be cut at an angle, rather than blunted or square cut, in order to facilitate introduction through the wall of the anterior chamber. The angled shape of the tip of the proximal portion allows the proximal portal to have a larger surface area to facilitate the flow of aqueous. The device should be at least capable of permitting the flow of aqueous humor at the estimated normal production rate of about 2.5 microliters per minute.

Figure 10:
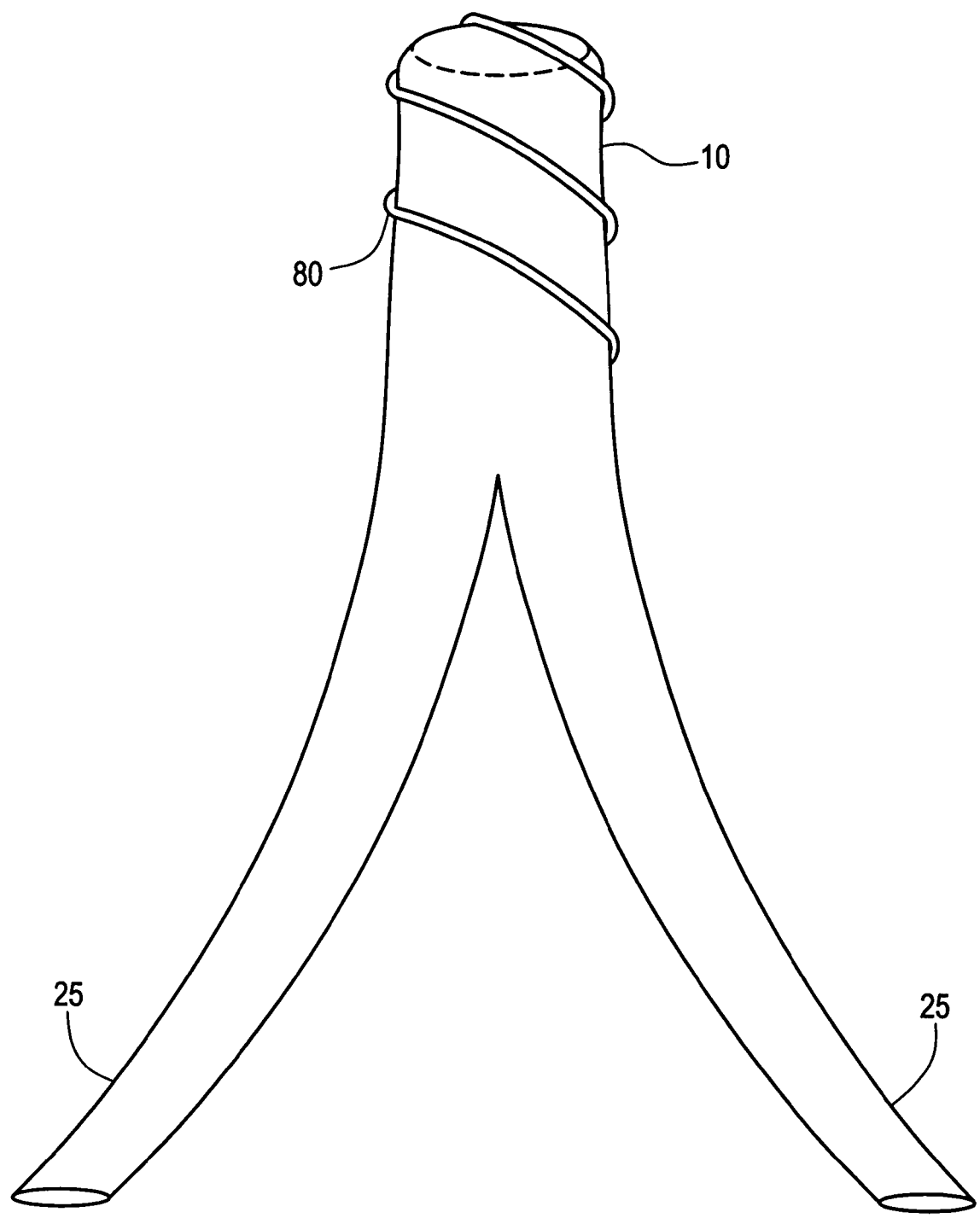
FIG. 10 shows another embodiment having a tapered proximal portion with screw threads.

FIG. 10 shows yet another embodiment of the device in which the proximal end comprises a larger single proximal lumen 10 which branches to form a pair of distal lumens 25 for insertion into Schlemm's canal. The proximal end is preferably tapered and contains screw threads 80 such that the device can be screwed into the anterior chamber and anchored therein by means of the threads and the distal ends inserted in Schlemm's canal. This embodiment would, in some instances, simplify insertion by eliminating the need to make an incision into the anterior chamber.

The anchor, as well as optionally the remainder of the device, can be constructed on a textured, grooved or porous material in order to facilitate the growth of cells, such as fibroblasts, to stabilize the implant from movement. Preferably, the extreme tips of the proximal and distal ends of the device are produced to avoid the attraction of new tissues, such as fibroblasts, which may grow at the surgical site and impede the flow of aqueous therethrough. Therefore, the proximal portion of the device can be produced to extend beyond the entrance into the anterior chamber by 0.1 to 3 mm, or preferably about 0.5 mm. As discussed above, the angled tip of the proximal portal will create a range of lengths along the proximal portion extending into the anterior chamber.

The distal portion(s) should similarly extend beyond the site of surgery and subsequent fibroblast proliferation. Therefore, the distal portion(s) can have a length of approximately 4 mm to 6 mm, again taking into consideration variability for angled extremities. The single or dual lumen shunt devices of the present invention can be manufactured by conventional molding or extrusion techniques. In the case of extrusion production, single lumens can be subsequently partially joined together to form dual lumen devices, or the individual lumens of a co-extruded dual lumen devices can be partially separated to define distal portions extendable in separate directions. It is preferable that such devices be constructed such that they will not kink when wrapped around a 0.25 mm object.

Optionally, the device may also include one or more visible markings on the device to assist in proper placement in the anterior chamber or Schlemm's canal. Markings on the distal ends could be used to confirm the distal ends are properly inserted in Schlemm's canal and markings on the proximal end would avoid over or under insertion into the anterior chamber.

Optionally, the device may be selectively coated or permeated with therapeutic agents as desired. For example, where ingrowth is desired for stability, certain growth factors may be present, whereas at the terminal portals where obstructions are to be avoided, certain antifibrotic agents may be present, such as 5-fluourouracil or mitomycin. The device may be more generally provided with coatings that are antibiotic, anti-inflammatory, or carboxylic anhydrase inhibitors. Agents that facilitate the degradation of collagen within the trabecular meshwork can also be employed.

The present invention provides methods for the implantation and use of the shunt devices. The surgical procedure necessary to insert the device requires an approach through a conjunctival flap. A partial thickness scleral flap is then created and dissected half-thickness into clear cornea. The posterior aspect of Schlemm's canal is identified and the canal is entered posteriorly. Schlemm's canal and/or the anterior chamber may be expanded and lubricated by injection of a viscoelastic and/or a mitotic agent. Suitable viscoelastic compositions and devices and methods for their injection into the eye are disclosed in U.S. Pat. No. 5,360,399 which is incorporated herein by reference. When using viscoelastic compositions as part of the present invention care should be taken to avoid over-expanding and rupturing Schlemm's canal. The proximal portion of the shunt is then inserted through the inner wall of Schlemm's canal and trabecular meshwork into the anterior chamber within the angle between the iris and the cornea. In some cases, as incision may be needed from Schlemm's canal through the trabecular meshwork into the anterior chamber to facilitate passage of the proximal portion therethrough. One arm of the distal portion of the shunt device is grasped and threaded into Schlemm's canal. In a similar fashion, the other arm of the distal portion of the shunt device (when present) is inserted into Schlemm's canal in the opposing direction from the first. The scleral flap and conjunctival wound are closed in a conventional manner.

The following procedure may be followed for the insertion of a bi-directional shunt within Schlemm's canal, in particular to insert an anchored shunt as disclosed onto a surgically prepared tissue shelf:

- Obtain general or local anesthesia. Preferably with either a retrobulbar or peribulbar injection of an anesthetic agent (lidocaine, bupivacaine, etc.).
- Scrub the periocular region with a surgically acceptable antiseptic such as povodine solution. Place a lid speculum.
- Make a fornix-based conjunctival incision at the limbus. Ensure hemostasis with either bipolar cautery or diathermy.
- Make a 3-4 mm×3-4 mm scleral flap, extending to a depth within approximately 100 of the choroid.
- Dissect the flap anteriorly to unroof the outer wall of Schlemm's canal.
- Continue the dissection along a more shallow plane to create a corneo-scleral shelf over the trabecular meshwork. At surgeon's discretion, place a stay suture through the scleral flap to hold it in position.
- At surgeon's discretion, dilate the opening to Schlemm's canal on both sides of the flap using a viscocanalostomy cannula and a viscoelastic agent (e.g., hyaluronate or hyaluronate/chondroitin sulfate).
- Make a paracentesis at the limbus distal to the surgical site.
- At surgeon's discretion, inject a viscoelastic agent and a miotic (carbachol or acetylcholine) into the anterior chamber to deepen the area.
- Remove the GMP Shunt from its case. Insert the distal portions of the shunt into the canal on both sides.
- Enter the anterior chamber along the corneo-scleral shelf using a keratome blade or a 21 gauge needle.
- Insert the proximal portion of the tube into the anterior chamber.
- Close the scleral flap with interrupted 10-0 nylon sutures. Initially, place one suture at the base and one each along the two sides. Bury the suture knots.
- Deepen the anterior chamber with balanced salt solution through the paracentesis.
- Test the scleral flap with a cellulose sponge. If there is leakage, place additional 10-0 nylon sutures to achieve a watertight closure.
- Close the conunctiva with appropriately sized absorbable sutures.
- Dress the eye with subconjunctival and/or topical broad-spectrum antibiotic and corticosteroid.
- Place a protective shield over the eye and tape the shield in place.

Results of Preclinical Study in Animal Eyes

Study Device

A study in 16 swine was performed using a shunt device comprising two (2) 7 mm length, 0.125 mm inner diameter and 0.250 mm outer diameter silicone (65 A durometer) tubes bonded together with silicone adhesive over a 1.0 mm length at the proximal end, creating a Y shape. The device was implanted in one eye of each animal and the non-implanted eye served as a control.

Surgical Procedure

For each animal, the periocular area of the study eye was prepped (eyelash trimming and betadine). The animal was then anesthesized using isofluorane. Under sterile conditions, a lid speculum was used to open the eyelids. An operating microscope was swung into place. A peripheral corneal bridle suture was placed to rotate the eye and expose the superior nasal limbus. A fornix-based conjunctival incision was made in the sclera and hemostasis ensured with bipolar cautery. A partial-thickness triangular scleral flap that measured 4×4 mm was made at the limbus and dissected anteriorly into clear cornea. A second, deeper flap was created at the base of the first flap, and dissected anteriorly to unroof the porcine equivalent of Schlemm's canal. The plane of the deeper flap then was angled anteriorly to create a corneoscleral shelf. A viscoelastic agent (hyaluronate and chondroitin sulfate) was instilled into the Schlemm's canal-like space on either side using a viscocanalostomy cannula. The distal aspects of the bi-directional glaucoma shunt were inserted into the canal on either side of the unroofing site. The anterior chamber was entered through the corneoscleral shelf and a viscoelastic agent instilled into the anterior chamber. The proximal (radial) portion of the shunt was inserted into the anterior chamber through the corneoscleral shelf. The scleral flaps were tightly closed with 10-0 nylon sutures and the knots buried. The conjunctiva was closed with absorbable suture. The bridle suture was removed. Subconjuctival garamycin and decadron were instilled interiorly. The eye was dressed with tobramycin-decadron ointment. The animal was allowed to awaken and returned to the boarding area.

In each case, the surgical endpoints were achieved. The Schlemm's canal-like space was accurately located and unroofed in 16 of 16 eyes and the device was successfully implanted without complication. Neither ocular structures nor the device were damaged during implantation. The surgical site was adequately closed without difficulty. During the procedure there was no observable touching between the device and the corneal endothelium, no collapse of the anterior chamber, no anterior chamber bleeding requiring washout, no tearing of the iris, and no touching between the device and the iris. All animals tolerated the surgery and anesthesia well.

Clinical Observations

All animals tolerated the implant procedure well. No animal demonstrated post-operative pain or discomfort as evidenced by rubbing, decreased eating or sleeping. No sight-threatening complications occurred due to implanting the device. Specifically, there was no chronic inflammatory reaction to the device, erosion of surrounding tissues, choroidal detachment or hemorrhage, retinal detachment, or infection.

The swine included in this study were normal animals without glaucoma. At baseline, the average intraocular pressures of the right and left eyes were equivalent. At 3 months post-operatively, the intraocular pressure in the study eye with the device was 14% lower than the contralateral (control) eye (n=16 animals).

It was unanticipated that IOP would drop in the study eyes since these eyes did not have glaucoma and therefore did not have an area of abnormal resistance to bypass. Nevertheless, the device resulted in a lower pressure even in these normal eyes. No eye had hypotony or ocular hypertension. Thus, in this interim phase of the study, the potential for pressure lowering of the device in a non-glaucomatous animal model was demonstrated.

Demonstration of in vivo Fluid Flow

At 3 months, two devices were explanted from two eyes for pressure-flow testing. In these eyes, a fornix-based conjunctival incision was made over the scleral flap. The scleral flap was gently loosened from the surrounding tissue and dissected forward to unroof the Schlemm's canal-like space. The device was identified within the space and the distal portions of the device were removed from the space, leaving the proximal portion within the anterior chamber. At this point, aqueous fluid was observed to flow through the shunt from the anterior chamber out of the distal tubes, demonstrating in vivo flow through the device.

While the above-described embodiments are exemplary, the invention contemplates a wide variety of shapes and configurations of the shunt to provide fluid communication between the anterior chamber and Schlemm's canal. The above-described embodiments are, therefore, not intended to be limiting to the scope of the claims and equivalents thereof.

The present invention is yet another means of treating glaucoma by enhancing the flow of aqueous fluid from the anterior chamber into Schlemm's canal. One of skill in the art will recognize that outflow must be balanced against production of new aqueous fluid such that near normal pressures of between approximately 15 mmHg and 21 mmHg are maintained. While lowering pressure is a goal, avoidance of hypotony (usually caused by pressures less than 6.0 mmHg) is also required for an effective treatment. It is readily apparent in one of skill in the art that the rate of fluid flow in the present device can be adjusted by increasing or decreasing the diameter of the device.

We claim:

1. A method of controlling the flow of aqueous humor in a living eye having an anterior chamber, a Schlemm's canal, and an episcleral venous system, the method comprising: introducing into the living eye an indwelling tubular body which leads from the anterior chamber into Schlemm's canal to provide an aqueous humor directing channel out of the anterior chamber; and draining aqueous humor through the tubular body to reduce intraocular pressure in the living eye.

2. The method of claim 1, wherein the flow rate of the aqueous humor is below about 2.5 microliters per minute.

3. The method of claim 1, wherein the flow rate of the aqueous humor is sufficient to maintain eye pressure above 6.0 mmHg.

4. The method of claim 1, wherein aqueous humor is produced by the eye at a rate that is about the same as the flow rate of aqueous humor through the tubular body.

5. The method of claim 1, wherein the flow rate maintains eye pressure between approximately 15 mmHg and 21 mmHg.

6. The method of claim 1, wherein aqueous humor is drained at a sufficient flow rate to reduce build-up of aqueous humor in the anterior chamber without hypotony.

7. The method of claim 6, wherein the flow rate is below about 2.5 microliters per minute.

8. The method of claim 1, wherein the tubular body comprises an arcuate outer surface.

9. The method of claim 1, wherein the tubular body comprises a cylindrical portion.

10. The method of claim 1, wherein the tubular body comprises a metal.

11. The method of claim 1, wherein the tubular body is dimensioned to allow non-linear fluid communication.

12. A method of controlling the flow of aqueous humor in a living eye having an anterior chamber, a Schlemm's canal, and an episcleral venous system, the method comprising: introducing a tubular body between Schlemm's canal and the anterior chamber, wherein the tubular body provides a first aqueous humor directing channel from the anterior chamber toward Schlemm's canal; and draining aqueous humor through the tubular body to reduce build-up of aqueous humor in the living eye.

13. The method of claim 12, wherein the tubular body provides a second aqueous humor directing channel from Schlemm's canal toward the episcleral venous system.

14. A method of controlling the flow of aqueous humor in a living eye having an anterior chamber, a Schlemm's canal, and an episcleral venous system, the method comprising: placing a substantially hollow device in the living eye leading from Schlemm's canal to the anterior chamber of the eye, wherein device provides an elongated aqueous humor directing channel within Schlemm's canal to guide the flow of aqueous humor from the anterior chamber toward the episcleral venous system, wherein the outer diameter of the portion of the device placed within Schlemm's canal is between about 0.1 mm and 0.5 mm; and draining aqueous humor along the elongated aqueous humor directing channel to maintain pressure above approximately 6.0 mmHg in the living eye.

15. The method of claim 14, wherein the flow rate maintains eye pressure between approximately 15 mmHg and 21 mmHg.

16. A method of controlling the flow of aqueous humor in a living eye having an anterior chamber, a Schlemm's canal, and an episcleral venous system, the method comprising: introducing a tubular body into Schlemm's canal and the anterior chamber to provide a non-linear aqueous humor directing channel from the anterior chamber toward the episcleral venous system; and draining aqueous humor through the tubular body at a sufficient flow rate to permit intraocular pressure to be reduced in the living eye.

17. The method of claim 16, wherein aqueous humor is drained at a sufficient flow rate to permit the reduction of intraocular pressure to no more than 21 mmHg.

18. The method of claim 16, wherein aqueous humor is drained at a sufficient flow rate to permit the reduction of intraocular pressure to establish a normal intraocular pressure for the eye.

19. The method of claim 16, wherein aqueous humor is drained at a sufficient flow rate to permit the regulation of intraocular pressure to no more than 21 mmHg.

20. The method of claim 16, wherein aqueous humor is drained at a sufficient flow rate to permit the regulation of intraocular pressure to establish a normal intraocular pressure for the eye.

21. A method of controlling the flow of aqueous humor in a living eye having an anterior chamber, a Schlemm's canal, and an episcleral venous system, the method comprising: providing a tubular body in Schlemm's canal comprising an elongated aqueous humor directing channel, wherein the outer diameter of the tubular body in Schlemm's canal is between about 0.1 mm and 0.5 mm, and the aqueous humor directing channel guides the flow of aqueous humor from the anterior chamber toward the episcleral venous system; and draining aqueous humor along the elongated aqueous humor directing channel at a sufficient flow rate to maintain pressure above approximately 6.0 mmHg in the living eye.

22. The method of claim 21, wherein the tubular body comprises a metal.

23. The method of claim 21, wherein the tubular body is non-linear.

* * * * *